United States Patent [19]

Goldiner et al.

[11] Patent Number: 5,569,036
[45] Date of Patent: Oct. 29, 1996

[54] CUSTOM FIT TEETH

[76] Inventors: Arthur Goldiner; Linda Camplese, both of 1565 Strand Way, Oceano, Calif. 93445

[21] Appl. No.: 236,380

[22] Filed: May 2, 1994

[51] Int. Cl.$^6$ .................................. A61C 13/02
[52] U.S. Cl. ................ 433/168.1; 433/180; 433/219
[58] Field of Search ................ 433/167, 168.1, 433/202.1, 180, 183, 219, 218, 171, 223; 472/133, 70

[56] References Cited

U.S. PATENT DOCUMENTS

| | | | |
|---|---|---|---|
| 2,057,341 | 10/1936 | Morgan | 433/168.1 |
| 3,558,540 | 1/1971 | Molnar . | |
| 4,251,215 | 2/1981 | May et al. | 433/168.1 |
| 5,324,198 | 6/1994 | Hazen | 433/167 |
| 5,403,186 | 4/1995 | Ginsburg | 433/167 |

OTHER PUBLICATIONS

Generik Ink, Inc., Why Not Party?® Custom Fangs, dated 1989.
Linda Camplese and Arthur Howard Goldiner, Custom Vampire Teeth, 1993.
Foothills Ltd., Custom Dracula Fangs and Custom Werewolf Fangs, dated 1994.
Violets, a division of RAM Southwest, Inc., Professional Fangtastics, 1996 Halloween Show Flyer.

*Primary Examiner*—Cary E. O'Connor
*Attorney, Agent, or Firm*—Harness, Dickey & Pierce

[57] ABSTRACT

Custom teeth, comprising molded acrylic, porcelain, ABS, or nylon artificial teeth, and an impression compound. Each anatomically disproportionate artificial tooth is molded in a predetermined shape and has an interior cavity. A user applies denture reliner material to the interior cavity and positions the artificial tooth on a existing human tooth while the liner cures and hardens. The custom teeth may then be removed and reused. The anatomically disproportionate teeth are colored, shaped, and polished to provide lifelike realism. Users can achieve a custom fit in about five minutes. One typical use is for cosmetic enhancement, such as vampire fangs. An alternate embodiment includes an artificial gum assembly with or without teeth installed and a resilient liner. The artificial tooth assembly is molded in a predetermined shape and has an internal cavity. Denture liner material is applied to the interior cavity and the artificial gum/tooth assembly is positioned on existing human teeth while the liner cures and hardens. The artificial tooth assembly may then be removed and reused.

21 Claims, 3 Drawing Sheets

10

CUSTOM FIT TEETH

CROSS REFERENCES TO RELATED APPLICATIONS

Molnar U.S. Pat. No. 3,558,540 (1971) is herein incorporated by reference. Molnar discloses a plastic impression compound. The compound provides for safe and quick dental impressions. The compound is formed by mixing a resin and a solvent, and sets in less than 15 minutes, and cures in less than an hour.

FIELD OF THE INVENTION

The present invention relates to artificial teeth. Lifelike costume fangs and an improved method of attachment are disclosed.

BACKGROUND

Several types of permanent artificial teeth are known. Dentures are used by people who have lost teeth. Bridges fill a gap formed by one or more missing teeth. Both dentures and bridges are custom molded to fit the teeth and mouth. The custom molding process takes several days and is very expensive. Dentures are typically made of acrylic or porcelain.

Wax has also been used to form artificial teeth for temporary cosmetic use such as at Halloween. Wax generally lacks the strength to withstand continued use, however.

Flexible plastic fangs, commercially available as Fang-tastiks™, are used to imitate Count Dracula. These fangs adhere to human teeth with a provided temporary and disposable over-the-counter adhesive, such as Sea-Bond™. The plastic does not appear realistic and does not adhere well.

Denture relining material is used to re-seat a denture after wear to avoid the cost of new dentures. It is also used to provide an immediate fit before dentures can be custom made. The denture relining material is a resilient plastic. One brand is Coe-Soft®, manufactured by GC America. Coe-Soft® is described in U.S. Pat. No. 3,558,540.

The present invention combines the best attributes of all known art by providing high quality realistic acrylic Count Dracula-like teeth in combination with denture reliner material and denture adhesive. The result is lifelike realism, custom fit, good adhesion, low cost, and quick set up.

SUMMARY OF THE INVENTION

The main object of the present invention is to provide realistic costume teeth.

Another object of the present invention is to provide fangs.

Another object of the present invention is to provide a custom fit for costume teeth, simply and quickly.

Another object of the present invention is to provide for artificial teeth that can be removed and reused.

Another object of the present invention is to provide a low cost construction of artificial teeth.

Other objects of this invention will appear from the following description and appended claims, reference being had to the accompanying drawings forming a part of this specification wherein like reference characters designate corresponding parts in the several views.

In the preferred embodiment an artificial tooth or fang is molded from a dental acrylic. Pigments are used for realistic color. The fang is molded in a standard shape; it is not custom fitted. The artificial, anatomically disproportionate teeth could also be made of porcelain, ABS plastic, (acrylonitrile-butadiene-styrene), or nylon.

The fang user prepares a liner for the inside of the plastic fang. A dental reliner, such as Coe-Soft®, available through dental distribution companies, is inserted in the fang and used for the liner. The user places the fang assembly 10 filled with uncured liner up onto a canine tooth, and allows it to remain for approximately five minutes. During that time, the liner 20 sets up to form a permanent, resilient impression of the user's tooth inside the tooth cap. The liner is then custom molded to the user's tooth by the user. The molding process takes about five minutes. Once the custom molding is complete, the fangs can be removed and reused. The fangs usually will stay in place without need for denture adhesive, although a small amount could be used. Generally, costume fangs are not intended to be worn while eating.

An artificial gum having teeth is shown as an alternate embodiment. The artificial gum is made of a flexible plastic that is custom fit by the user with the same liner as the fang product.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DETAILED DESCRIPTION OF THE PREFERRED EMBODIMENT

Figure 1:
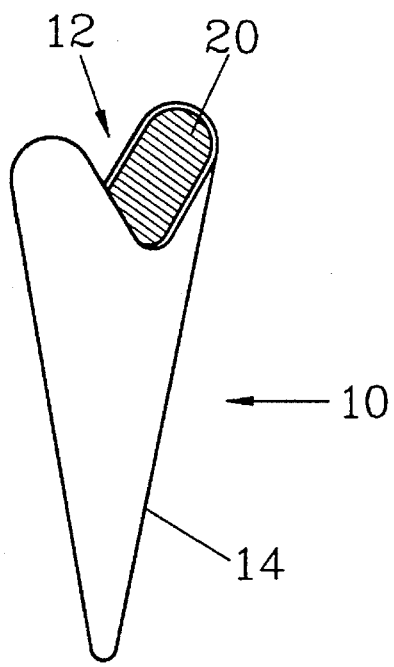
FIG. 1 is a perspective view of a fang.
Figure 2:
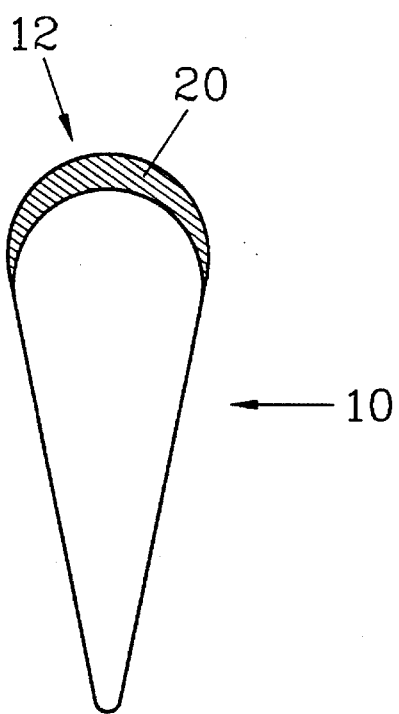
FIG. 2 is a back view of a fang.
Figure 3:
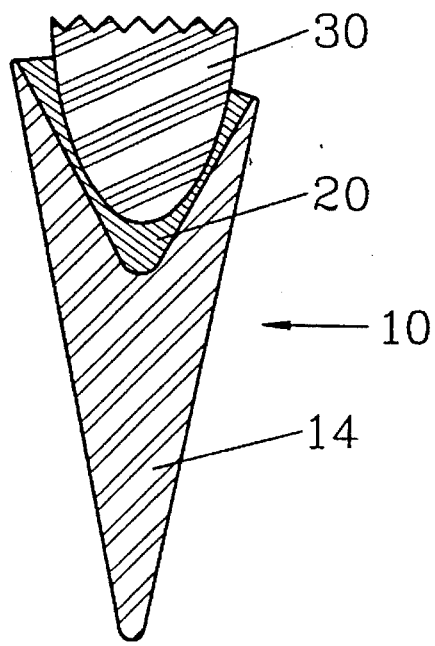
FIG. 3 is a cross section of a fang as seen from 3—3 in FIG. 4.

Referring first to FIGS. 1–3, a fang assembly 10 is shown. The fang assembly 10 has a molded plastic fang 14 and a liner 20. The plastic and liner are available from chemical distributors and dental product companies. Pigments are used to create a realistic look. The plastic fang 14 is molded with an interior cavity 12 which roughly fits over a user's canine tooth. The interior cavity 12 of the fang 10 is not meant to fit tightly.

The interior cavity 12 is filled with a pre-measured amount of liner 20. The liner 20 is mixed by the user and added to the fang 10 by the user and provides a custom fit to the user's canine tooth. Users may optionally use a thin layer of denture adhesive to enhance adherence and further prevent the fang 10 from coming off.

Liner 20 is available from dental supply companies in several different varieties. It is known as an impression compound or denture relining material. Typically it is supplied in two parts—a powder and a liquid. When mixed, a non-tacky gel is formed. The gel generally goes through 3 stages: a wetting stage; an impression-taking or mold-making stage; and a molding stage. The gel transitions to the mold-making stage a few minutes after mixing the components. The gel hardens, or sets, in about five minutes. Once hardened, the denture relining retains its shape but is resilient.

The user is provided with the molded plastic fang 14 and the liner powder and liquid. The user first finds an accommodating location in his mouth for the fang 14. Next, the user mixes the liner components to form a gel. The gel is applied to the interior cavity 12 of the plastic fang 14. The fang assembly 10 is then placed over one of the user's canine teeth 30, or in some other selected location, and held in the desired position for about five minutes. Then the fang assembly 10 is removed from the tooth. Preferably, the liner 20 is allowed to cure for another 45 minutes. The liner 20 is then permanently attached to the interior cavity 12 of the plastic fang 14. One or more additional fangs can be prepared in an identical fashion.

The plastic fangs 14 are polished on the outside to achieve a realistic appearance. The interior cavity 12 has a rough surface to enhance adhesion of the liner 20.

There are several desirable properties for the liner 20. The liner must set within a reasonable short time so that the assembly may be removed. In practice, it is difficult to hold something in a mouth for more than about 5 minutes without moving positions. The liner must also not set too quickly. The user must have time to position the assembly before the set occurs. The liner should thus have a quick but controlled setting time.

Additionally, the liner has to be reasonably easy to use, or many users would not be able to use the liner. The liner should not irritate the skin, have an unpleasant odor, or be water soluble. These qualities might preclude placement in a mouth.

The preferred liner that satisfies these requirements is Coe-Soft®, available from GC America. It is a plastic impression compound, described in U.S. Pat. No. 3,558,540. The liner is comprised of two components: a solid resin and a solvent system. Typical resins include ethyl methacrylate. Extenders are used to extend and control the setting time, as well as the tackiness. Extenders include edible vegetable oils and alkylhydrocarbons. A plasticizer such as a dibutyl phthalate is also used.

Used to make the teeth for the dentures is Fixacryl™ Cold Cure Acrylic from Esschem Company. It is a poly methacrylate compound that includes: dialkyl phthalate, fibers, pigments, and other compounds. The compound can also be used to make fang toothcaps. Alternatively, these toothcaps can be injection molded of either ABS plastic or nylon.

Figure 4:
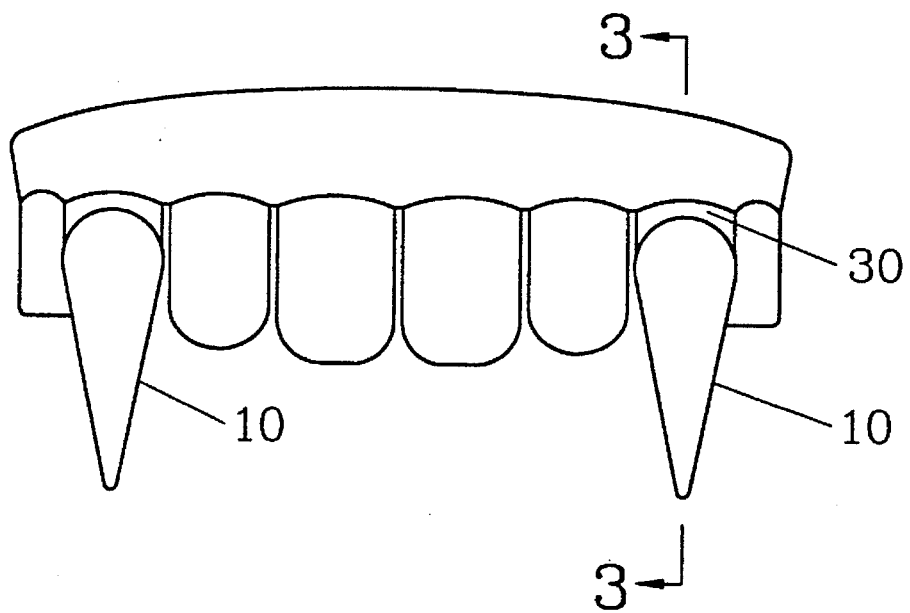
FIG. 4 is a front view of a fang-equipped mouth.

Referring next to FIG. 4, a pair of fangs is shown in a mouth. The fang assemblies 10 have been placed on the canine teeth 30 of the mouth. Although the preferred embodiment is for use as fangs, such as would be needed for vampire role-playing, other cosmetic uses could be accomplished with the present invention. The uses would include creating other desired themes for artificial teeth such as a werewolf, robot, mutant, movie character, or other appearance.

Figure 5:
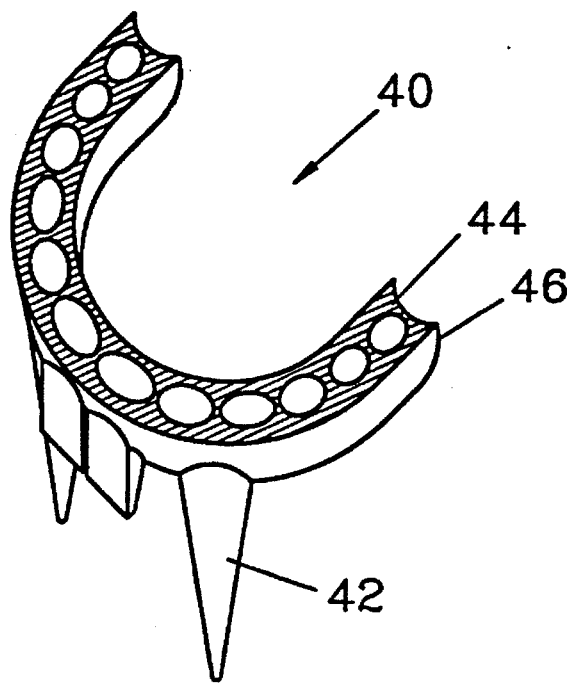
FIG. 5 is a perspective view of artificial teeth with a gum.
Figure 6:
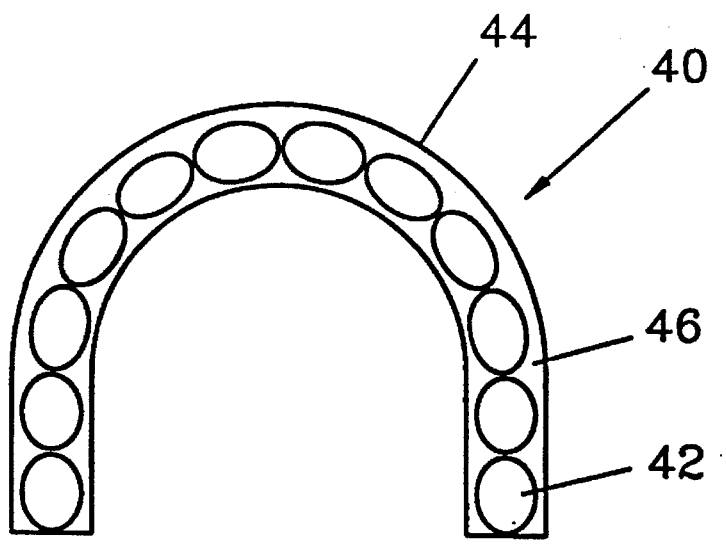
FIG. 6 is a top view of artificial teeth with a gum.

Referring next to FIGS. 5–6, an artificial tooth and gum assembly 40 is shown. The tooth and gum assembly 40 includes artificial teeth 42, artificial gum 44, and liner 46.

The teeth 42 can be made of porcelain, acrylic, another plastic, or nylon. The teeth are pre-formed, and molded to predetermined shapes.

A standard artificial gum 44 embedded with teeth is provided to fit over real teeth. Alternatively, an artificial gum can be provided without teeth. The gum 44 is a flexible plastic, provided in two parts. The plastic is commercially available from Confi-Dental Products Company. The powder comprises polyethylmethacrylate, pigments, and benzoyl peroxide. Pigments can provide a human gum color. The liquid comprises alkylmethacrylate, dialkyl phthalate, dimethyl p-toludine, and hydroquinone. The chemical composition is similar to that of the liner.

The user is provided with a standard artificial gum, usually embedded with artificial teeth, and a liner resin and solvent. The user prepares a liner for the inside of the denture. The liner compound used is identical to that of the liner 20 as shown in FIGS. 1–3. The user mixes the liner resin (a powder) and the liner solvent system (a liquid) together to form a liner gel. The user then fills the interior cavity of the molded gum 44 with the previously mixed liner gel.

The gum with the uncured liner gel is then placed over the user's teeth. After about 5 minutes, the liner 20 sets up to form a permanent resilient impression of the user's bite registration inside the denture. The entire gum assembly can then be removed, since the liner will have set sufficiently by this time. Preferably the liner is allowed to cure for an additional 45 minutes.

The gum assembly 40 can be used repetitively. Some users may find a denture adhesive helpful in stabilizing the gum assembly and preventing the gum assembly from falling off.

Through the use of pigments, a flexible standard gum-line and realistic pre-molded teeth, and the custom fit process, the present invention provides the user with custom fit teeth of higher quality at lower cost and with a shorter preparation time than is available with any known prior art. With the present invention, any user can install and remove custom costume teeth faster than a real werewolf or vampire.

Although the present invention has been described with reference to preferred embodiments, numerous modifications and variations can be made and still the result will come within the scope of the invention. No limitation with respect to the specific embodiments disclosed herein is intended or should be inferred.

We claim:

1. A method of preparing an anatomically disproportionate artificial tooth apparatus for use in a human mouth with human teeth, comprising the steps of:
   (a) molding an anatomically disproportionate artificial tooth having an interior cavity;
   (b) thereafter inserting an impression compound into said interior cavity;
   (c) thereafter coating said interior cavity with said impression compound forming a liner whereby an anatomically disproportionate artificial tooth assembly is formed;
   (d) thereafter positioning said anatomically disproportionate artificial tooth assembly over at least one of said human teeth in said mouth;
   (e) thereafter waiting 3 to 10 minutes with said anatomically disproportionate artificial tooth assembly in position whereby said impression compound sets; and
   (f) thereafter removing said anatomically disproportionate artificial tooth assembly from said mouth.

2. The method of claim 1, further comprising the steps of:
   (a) applying denture adhesive to said liner after removal from said mouth;
   (b) thereafter positioning said anatomically disproportionate artificial tooth assembly over said human teeth.

3. An anatomically disproportionate artificial tooth apparatus produced in accordance with claim 1.

4. The method of claim 1, wherein said anatomically disproportionate artificial tooth assembly comprises a material selected from the group consisting of acrylic plastic, ABS (acrylonitrile-butadiene-styrene) plastic, thermoforming plastic, polyethylene, polypropylene, porcelain, and nylon.

5. The method of claim 1, wherein said anatomically disproportionate artificial tooth assembly consists essentially of a fang-shaped artificial tooth.

6. The method of claim 1 wherein the anatomically disproportionate artificial tooth assembly further comprises an artificial gum.

7. The method of claim 6, wherein the method of preparing the artificial gum comprises the steps of:
(a) mixing a gum resin and a gum solvent to form a gum gel; and
(b) embedding said anatomically disproportionate artificial teeth in said gum gel.

8. An artificial cosmetic tooth assembly for use in a mouth over existing human teeth, comprising:
at least one anatomically disproportionate artificial tooth having an interior cavity; and
a liner, prepared by utilizing an impression compound to form a liner, placing said liner in said interior cavity, placing said anatomically disproportionate artificial tooth with said liner over said existing human teeth, waiting for said liner to set whereby a custom impression of said existing human teeth is formed, and removing said anatomically disproportionate artificial teeth from said mouth.

9. The artificial cosmetic tooth assembly of claim 8, wherein:
said anatomically disproportionate artificial teeth being embedded in an artificial gum assembly; and
said gum assembly being prepared by:
(a) mixing a resin and a solvent to form a non-tacky gum gel;
(b) positioning said anatomically disproportionate teeth in standard mold;
(c) placing said gum gel into said standard mold;
(d) waiting for said gum gel to set, whereby a flexible elastomeric artificial gum is formed, and;
(e) removing said gum assembly from said standard mold.

10. The artificial cosmetic tooth assembly of claim 8 wherein said liner comprises a partial plate.

11. The artificial cosmetic tooth assembly of claim 8 wherein said at least one anatomically disproportionate artificial tooth comprises at least one incisor.

12. The artificial cosmetic tooth assembly of claim 8 wherein said at least one anatomically disproportionate artificial tooth comprises a set of upper teeth.

13. The artificial cosmetic tooth assembly of claim 12 wherein said set of upper teeth are equal in size and shape.

14. An artificial cosmetic tooth assembly for placement over human teeth, comprising:
at least one anatomically disproportionate artificial tooth having an interior cavity; and
a liner, prepared by impressing an impression compound between the interior cavity of said artificial tooth and said human teeth, whereby a custom fit is provided.

15. The assembly of claim 14, wherein said anatomically disproportionate artificial tooth assembly further comprises a material selected from the group consisting of acrylic plastic, ABS (acrylonitrile-butadiene-styrene) plastic, nylon, and porcelain.

16. The apparatus of claim 14, wherein said impression compound comprises a mixture of a resin and a solvent.

17. The apparatus of claim 16, wherein:
said resin comprises a thermoplastic granular lower-alkyl methacrylate copolymer;
said solvent comprises from about 10 to 50 volume percent alcohol;
said solvent further comprises an oil extender, whereby the set time of said impression compound is extended; and said solvent further being present from about 5 to about 12 cc. per 10 grams of said resin.

18. The apparatus of claim 14, wherein said anatomically disproportionate artificial tooth assembly consists essentially of a substantially fang-shaped artificial tooth.

19. The apparatus of claim 14, wherein said anatomically disproportionate artificial tooth assembly further comprises an artificial gum.

20. The apparatus of claim 19, wherein:
said artificial gum is prepared by the steps of:
(a) placing anatomically disproportionate artificial teeth in a mold;
(b) mixing a gum resin and a gum solvent to form a gum gel;
(c) placing said gum gel in said mold, and;
(d) removing said artificial gum from said mold after 20 to 30 minutes whereby said gum gel has cured.

21. The artificial cosmetic tooth assembly of claim 14 wherein said liner comprises a partial plate.

* * * * *